United States Patent
Horan et al.

(10) Patent No.: US 10,197,579 B2
(45) Date of Patent: Feb. 5, 2019

(54) METHODS FOR MEASUREMENT OF INHIBITION OF C-JUN N-TERMINAL KINASE IN SKIN

(71) Applicant: Signal Pharmaceuticals, LLC, San Diego, CA (US)

(72) Inventors: Gerald Scott Barden Horan, Winchester, MA (US); Ying Ye, Branchburg, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 145 days.

(21) Appl. No.: 15/335,624

(22) Filed: Oct. 27, 2016

(65) Prior Publication Data

US 2017/0045531 A1    Feb. 16, 2017

Related U.S. Application Data

(62) Division of application No. 14/969,744, filed on Dec. 15, 2015, now Pat. No. 9,513,297.

(60) Provisional application No. 62/092,531, filed on Dec. 16, 2014.

(51) Int. Cl.
*A61K 31/505* (2006.01)
*G01N 33/68* (2006.01)
*A61K 9/00* (2006.01)
*G01N 33/50* (2006.01)

(52) U.S. Cl.
CPC ....... *G01N 33/6881* (2013.01); *A61K 9/0053* (2013.01); *A61K 31/505* (2013.01); *G01N 33/5008* (2013.01); *G01N 33/5082* (2013.01); *G01N 2333/4706* (2013.01); *G01N 2333/91205* (2013.01); *G01N 2440/14* (2013.01); *G01N 2800/20* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,845,055 A | 10/1974 | Hoegerle et al. | |
| 6,432,963 B1 | 8/2002 | Hisamichi et al. | |
| 7,169,798 B2 | 1/2007 | Green et al. | |
| 7,449,456 B2 | 11/2008 | Nagashima et al. | |
| 7,517,886 B2 | 4/2009 | Singh et al. | |
| 7,524,849 B2 | 4/2009 | Zhang et al. | |
| 7,589,200 B2 | 9/2009 | Singh et al. | |
| 7,601,714 B2 | 10/2009 | Barbosa, Jr. et al. | |
| 7,718,653 B2 | 5/2010 | Barlaam et al. | |
| 7,893,074 B2 | 2/2011 | Garcia-Echeverria et al. | |
| 7,956,060 B2 | 6/2011 | Arai et al. | |
| 8,338,439 B2 | 12/2012 | Singh et al. | |
| 8,513,242 B2 | 8/2013 | Chiang et al. | |
| 8,519,129 B2 | 8/2013 | Marsilje, III et al. | |
| 8,580,805 B2 | 11/2013 | Maehr | |
| 8,853,230 B2 | 10/2014 | Bauer et al. | |
| 8,969,336 B2 | 3/2015 | Shimada et al. | |
| 9,139,534 B2 | 9/2015 | Bennett et al. | |
| 9,365,524 B2 | 6/2016 | Man et al. | |
| 2008/0139531 A1 | 6/2008 | Yanni et al. | |
| 2009/0036440 A1 | 2/2009 | Barlaam et al. | |
| 2011/0130415 A1 | 6/2011 | Singh et al. | |
| 2011/0159019 A1 | 6/2011 | Tanaka et al. | |
| 2016/0096841 A1 | 4/2016 | Alexander et al. | |
| 2016/0168105 A1 | 6/2016 | Boersen et al. | |

FOREIGN PATENT DOCUMENTS

| | | |
|---|---|---|
| EP | 1 184 376 | 3/2002 |
| EP | 1 518 855 | 3/2005 |
| JP | 2006/124387 | 5/2006 |
| WO | WO 1999/31073 | 6/1993 |
| WO | WO 2000/12485 | 3/2000 |
| WO | WO 2000/76980 | 12/2000 |
| WO | WO 2003/063794 | 8/2003 |
| WO | WO 2003/078404 | 9/2003 |
| WO | WO 2003/082855 | 9/2003 |
| WO | WO 2004/014382 | 2/2004 |
| WO | WO 2004/054617 | 7/2004 |
| WO | WO 2004/002964 | 8/2004 |
| WO | WO 2004/067516 | 8/2004 |
| WO | WO 2006/027377 | 3/2006 |
| WO | WO 2006/027378 | 3/2006 |
| WO | WO 2006/035069 | 4/2006 |

(Continued)

OTHER PUBLICATIONS

Pfundt et al. J. Pathology 2001 vol. 193, p. 248-255 (Year: 2001).*
Kim et al. J. Lipid Research 2006 vol. 47, (Year: 2006).*
Adeyeye, M. C. et al. (Eds.), *Preformulation in Solid Dosage Form Development*, CRC Press, 2008, pp. 239-240.
Bogoyevitch et al., 2010, "c-Jun N-terminal kinase (JNK) signaling: Recent advances and challenges," Biochimica et Biophysica Acta 1804:4630475.
Bosseray et al., PubMed Abstract (Pathol Biol (Paris) 50(8):483-92), Oct. 2002.

(Continued)

Primary Examiner — Changhwa J Cheu
(74) Attorney, Agent, or Firm — Jones Day

(57) ABSTRACT

Provided herein are methods for evaluating the effect of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof in a patient with an assay based on UVB-irradiation and phosphorylated c-Jun expression. The analyses allow for evaluation of dose-response and identification of patient populations who are sensitive to 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof.

6 Claims, 5 Drawing Sheets

(56) References Cited

FOREIGN PATENT DOCUMENTS

| | | |
|---|---|---|
| WO | WO 2006/091737 | 8/2006 |
| WO | WO 2008/009458 | 1/2008 |
| WO | WO 2008/129380 | 10/2008 |
| WO | WO 2009/012421 | 1/2009 |
| WO | WO 2009/131687 | 10/2009 |
| WO | WO 2009/136995 | 11/2009 |
| WO | WO 2009/143389 | 11/2009 |
| WO | WO 2009/145856 | 12/2009 |
| WO | WO 2009/158571 | 12/2009 |
| WO | WO 2010/024430 | 3/2010 |
| WO | WO 2010/032875 | 3/2010 |
| WO | WO 2010/038081 | 4/2010 |
| WO | WO 2010/051223 | 5/2010 |
| WO | WO 2010/080864 | 7/2010 |
| WO | WO 2010/090875 | 8/2010 |
| WO | WO 2010/097248 | 9/2010 |
| WO | WO 2010/129802 | 11/2010 |
| WO | WO 2010/144468 | 12/2010 |
| WO | WO 2011/016472 | 2/2011 |
| WO | WO 2011/065800 | 6/2011 |
| WO | WO 2011/090760 | 7/2011 |
| WO | WO 2012/012619 | 1/2012 |
| WO | WO 2012/044936 | 4/2012 |
| WO | WO 2012/045010 | 4/2012 |
| WO | WO 2012/045020 | 4/2012 |
| WO | WO 2012/145569 | 4/2012 |
| WO | WO2012/061057 | 5/2012 |

OTHER PUBLICATIONS

Bundgaard, "Design of prodrugs: Bioreversible derivatives for various functional groups and chemical entities," Design of Prodrugs, Chapter 1, p. 1, 1985.
Cohen P. 2001, "The role of protein phosphorylation in human health and disease." The Sir Hans Krebs Medal Lecture. Eur J Biochem. 268(19):5001-10.
Cohen P. 2002, "Protein kinases—the major drug targets of the twenty-first century?" Nat Rev Drug Discov. 1(4):309-15.
Das et al., 1996, "Activation of raf-1, MEK, and MAP kinase in prolactin responsive mammary cells," Breast Cancer Res. Treat., 40(2):141-149.
Davis RJ., 1994, "MAPKs: new JNK expands the group." Trends Biochem Sci., 19(11):470-3.
Douglas, Jr., 1996, "Introduction to Viral Diseases," Cecil Textbook of Medicine, 20th Edition, vol. 2, pp. 1739-1747.
Eferl et al., 2008, "Development of pulmonary fibrosis through a pathway involving the transcription factor Fra-2/AP-1," PNAS, 105(30):10525-10530.
Fanger et al., 1997, "MEKKs, GCKs, MLKs, PAKs, TAKs, and tpls: upstream regulators of the c-Jun amino-terminal kinases?" Curr Opin Genet Dev. 7(1):67-74.
Gaestel et al., 2007, "Protein kinases as small molecule inhibitor targets in inflammation." Curr Med Chem. 14(21):2214-34.
Goff, PubMed Abstract (J Gene Med 3(6):517-28), No-Dec. 2001.
Grimminger et al., 2010, "Targeting non-malignant disorders with tyrosine kinase inhibitors," Nat Rev Drug Sisc., 9(12):956-970.
Hirabayashi et al., 2008, "A novel Syk family kinase inhibitor: design, synthesis, and structure-activity relationship of 1,2,4-triazolo[4,3-c]pyrimidine and 1,2,4-triazolo[1,5-c]pyrimidine derivatives," Bioorg Med Chem., 16:7347-7357.
Hirosumi et al., 2002, "A central role for JNK in obesity and insulin resistance," Nature, 420:333-336.
Hisamichi et al., 2005, "Synthetic studies on novel Syk inhibitors. Part 1: Synthesis and structure-activity relationships of pyrimidine-5-carboxamide derivatives," Bioorg Med Chem., 13:4936-4951.
Hisamichi et al., 2005, "Corrigendum to Synthetic studies on novel Syk inhibitors. Part 1: Synthesis and structure-activity relationships of pyrimidine-5-carboxamide derivatives," Bioorg. Med. Chem., 13:6277-6279.

Hu et al., 2000, "Prolonged activation of the mitogen-activated protein kinase pathway is required for macrophage-like differentiation of a human myeloid leukemic cell line," Cell Growth Differ., 11(4):191-200.
Hulikal, "L15 Deuterium Labeled Compounds in Drug Discovery Process," Abstract, 2010.
Ichijo H., 1999, "From receptors to stress-activated MAP kinases." Oncogene. 18(45):6087-93.
Jones et al., 2012, Phase 1 Results From a Study of Romidepsin in Combination With Gemcitabine in Patients With Advanced Solid Tumors, Cancer Investigation, 30:481-486.
Kaneto et al., 2007, "Oxidative stress and the JNK pathway are involved in the development of type 1 and type 2 diabetes," Curr Mol Med., 7:674-686.
Katayama et al., 2008, "Identification of a key element for hydrogen-bonding patterns between protein kinases and their inhibitors," Proteins, 73:795-801.
Kluwe et al., 2010, "Modulation of hepatic fibrosis by c-Jun-N-terminal kinase inhibition," Gastroenterology 138:347-359.
Kodama et al., 2009, "c-Jun N-terminal kinase-1 from hematopoietic cells mediates progression from hepatic steatosis to steatohepatitis and fibrosis in mice," Gastroenterology, 137:1467-1477.e5.
Kyriakis JM., 2000, "MAP kinases and the regulation of nuclear receptors." Sci STKE. (48):pe1.
Le Jeune et al., 2006, "Evaluation of imatinib mesylate effects on glioblastoma aggressiveness with SPECT radiotracer 99mTc-(v)-DMSA." Eur J Cancer. 42(8):1004-13.
Liddle et al., 2011, "Discovery of GSK143, a highly potent, selective and orally efficacious spleen tyrosine kinase inhibitor," Bioorg Chem Chem Lett., 21:6188-6194.
Malhi et al., 2006, "Free fatty acids induce JNK-dependent hepatocyte lipoapoptosis," J Biol Chem., 281:12093-12101.
Malhi et al., 2008, "Molecular mechanisms of lipotoxicity in nonalcoholic fatty liver disease," Semin Liver Dis., 28(4):360-369.
Nagashima et al., 2007, "Synthesis and evaluation of 2-{[2-(4-hydroxyphenyl)-ethyl]amino}pyrimidine-5-carboxamide derivatives as novel STAT6 inhibitors," Bioorg Med Chem., 15:1044-1055.
Nagashima et al., 2008, "Identification of 4-benzylamino-2-[(4-morpholin-4-ylphenyl)amino]pyrimidine-5-carboxamide derivatives as potent and orally bioavailable STAT6 inhibitors," Biorg Med Chem., 16:6509-6521.
Nagashima et al., 2009, "Novel 7H-pyrrolo[2,3-d]pyrimidine derivatives as potent and orally active STAT6 inhibitors," Bioorg Med Chem., 17:6926-6936.
Ohga et al., 2008, "YM-341619 suppresses the differentiation of spleen T cells into Th2 cells in vitro, eosinophilia, and airway hyperresponsiveness in rat allergic models," Eur J Pharmacol., 590:409-416.
Papp et al., 2007, "Steady state kinetics of spleen tyrosine kinase investigated by a real time fluorescence assay," Biochemistry, 46:15103-15114.
Pimlott, PubMed Abstract (Nucl Med Commun. 26(3):183-8), 2005.
Razonable et al., PubMed Abstract (Herpes 10(3):60-5), Dec. 2003.
Reilly et al., 2011, "PRT-060318, a novel Syk inhibitor, prevents heparin-induced thrombocytopenia and thrombosis in a transgenic mouse model," Blood, 117(7):2241-2246.
Sanam et al., 2009, "Discovery of potential ZAP-70 kinase inhibitors: pharmacophore design, database screening and docking studies," Eur J Med Chem., 44:4793-4800.
Sanchez-Tillo et al., 2007, "JNK1 Is required for the induction of Mkp1 expression in macrophages during proliferation and lipopolysaccharide-dependent activation," J Biol Chem., 282(17):12566-73.
Schramek H., 2002, "MAP kinases from intracellular signals to physiology and disease." News Physiol Sci. 17:62-7.
Schwabe et al., 2004, "Differential requirement for c-Jun NH2-terminal kinase in TNF-α- and Fas-mediated apoptosis in hepatocytes," FASEB J. 18(6):720-722.
Seger and Krebs, 1995, "The MAPK signaling cascade." FASEB J. 9(9):726-35.
Silverman, 1992, "Prodrugs and Drug Delivery Systems," The Organic Chemistry of Drug Design and Drug action, Chapter 8, pp. 352-400.

(56) References Cited

OTHER PUBLICATIONS

Singh et al., 2009, "Differential effects of JNK1 and JNK2 inhibition on murine steatohepatitis and insulin resistance," Hepatology, 49(1):87-96.

Singh et al., 2012, "Discovery and development of spleen tyrosine kinase (SYK) inhibitors," J Med Chem., 55:3614-1643.

Sridhar et al., 2000, "Protein kinases as therapeutic targets," Pharm Res., 17(11):1345-1353.

Storey, R. A. et al. (Eds.), *Solid State Characterization of Pharmaceuticals*, Wiley-Blackwell, 2011, pp. 473-491, 490.

Uehara et al., 2004, "c-Jun N-Terminal Kinase Mediates Hepatic Injury after Rat Liver Transplantation," Transplantation, 78(3):324-332.

Vallerie et al., 2010, "The role of JNK proteins in metabolism," Sci Transl Med., 2(60):1-7.

Villasenor et al., 2009, "Structural insights for design of potent spleen tyrosine kinase inhibitors from crystallographic analysis of three inhibitor complexes," Chem Biol Drug Des., 73:466-470.

Virkamaki et al., 1999, "Protein-protein interaction in insulin signaling and the molecular mechanisms of insulin resistance," J Clin Invest., 103(7):931-943.

Whitmarsh AJ, et al. 1999, "Signal transduction by MAP kinases: regulation by phosphorylation-dependent switches." Sci. STKE. (1):pe1.

Xie et al., 2009, "Pharmacophore modeling study based on known spleen tyrosine kinase inhibitors together with virtual screening for identifying novel inhibitors," Bioorg Med Chem Lett., 19:1944-1949.

Alcorn et al., 2009, "c-Jun N-Terminal Kinase 1 Is Required for the Development of Pulmonary Fibrosis", Am. J. Respir. Cell. Mol. Biol., vol. 40: 422-432.

Davis, Roger J., 2000, "Signal Transduction by the JNK Group of MAP Kinases", Cell, vol. 103: 239-252.

Lee et al., 2005, "Bleomycin induces alveolar epithelial cell death through JNK-dependent activation of the mitochondrial death pathway", Am. J. Physiol. Lung Cell. Mol. Physiol., 289: L521-L528.

Lin et al., 2013, "Connective tissue growth factor induces collagen I expression in human lung fibroblasts through the Rac1/MLK3/JNK/AP-1 pathway", Biochimica et Biophysica Acta, 1833: 2823-2833.

Yoshida et al., 2002, "MAP kinase activation and apoptosis in lung tissues from patients with idiopathic pulmonary fibrosis", J. Pathol., 198: 388-396.

\* cited by examiner

METHODS FOR MEASUREMENT OF INHIBITION OF C-JUN N-TERMINAL KINASE IN SKIN

This application is a divisional of U.S. application Ser. No. 14/969,744, filed Dec. 15, 2015, currently allowed, which claims the benefit of U.S. Provisional Application No. 62/092,531, filed Dec. 16, 2014, the contents of which are incorporated by reference herein in their entirety.

1. FIELD

Provided herein are methods for measuring the inhibition of c-Jun N-terminal kinase (JNK) in skin using immunohistochemistry. Further provided herein is an assay based on UVB-irradiation and measurement of phospho c-Jun (or phosphorylated c-Jun) immunoreactivity useful for evaluating dose-response relationships of 2-(tert-butylamino)-4-((1R,3R,4R)-3-hydroxy-4-methylcyclohexylamino)-pyrimidine-5-carboxamide and identifying and selecting patient populations sensitive or insensitive to 2-(tert-butylamino)-4-((1R,3R,4R)-3-hydroxy-4-methylcyclohexylamino)-pyrimidine-5-carboxamide.

2. BACKGROUND

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.* 14: 2214-223 (2007); Grimminger et al. *Nat. Rev. Drug Disc.* 9(12):956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

JNK is a ubiquitously expressed serine/threonine kinase belonging, together with ERK (extracellular-regulated kinase) and p38, to the family of mitogen-activated protein kinases (MAPKs). Kyriakis J M, *Sci. STKE* (48):pe1 (2000); Whitmarsh A J, et al. *Sci. STKE* (1):pe1 (1999); Schramek H, *News Physiol. Sci.* 17:62-7 (2002); Ichijo H, *Oncogene* 18(45):6087-93 (1999). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates nonnuclear proteins, for example, IRS-1, and Bcl-2 family members. Davis R J, *Trends Biochem. Sci.* 9(11):470-473 (1994); Seger R et al., *FASEB J.*; 9(9):726-35 (1995); Fanger G R et al., *Curr. Opin. Genet. Dev.*; 7(1):67-74 (1997).

The mitogen activated protein (MAP) kinases participate in the transduction of signals to the nucleus of the cell in response to extracellular stimuli. Examples of MAP kinases from the ERK p38 and JNK isoforms include but are not limited to, mitogen-activated protein kinase 1 (ERK2), mitogen-activated protein kinase 8 (JNK1), mitogen-activated protein kinase 9 (MAPK9 or JNK2), mitogen-activated protein kinase 10 (MAPK10 or JNK3) and mitogen-activated protein kinase 14 (MAPK14 or p38alpha). MAP kinases are a family of proline-directed serine/threonine kinases that mediate signal transduction from extracellular receptors or heat shock, osmotic stress, reactive oxidant species (ROS) or UV radiation. See Sridhar et al., *Pharmaceutical Research*, 17:11 1345-1353 (2000). MAP kinases are activated via the phosphorylation of theonine and tyrosine by upstream dual-specificity protein kinases, including MKK and MEKK kinases. Cell proliferation and differentiation have been shown to be under the regulatory control of multiple MAP kinase cascades. See Sridhar et al., *Pharmaceutical Research*, 17:11 1345-1353 (2000). As such, the MAP kinase pathway plays critical roles in a number of disease states. For example, defects in activities of MAP kinases have been shown to lead to aberrant cell proliferation and carcinogenesis. See Hu et al., *Cell Growth Differ.* 11:191-200 (2000); and Das et al., *Breast Cancer Res. Treat.* 40:141 (1996). Moreover, MAP kinase activity has also been implicated in insulin resistance associated with type-2 diabetes and obesity. See Virkamaki et al., *J. Clin. Invest.* 103:931-943 (1999). Changes in insulin resistance may have a direct impact on the metabolism of glucose and lipid in the liver contributing to the development of steatosis that may progress to liver fibrosis. See Vallerie et al. *Science Translational Medicine* 2(60): 1-7 (2010).

Steatosis may develop in the presence of either saturated or unsaturated free fatty acids (FFA). FFA promote robust JNK activation in liver and excessive concentrations of FFA may lead to hepatocyte apoptosis. It has been reported that JNK2−/− mice are partially protected from steatosis and apoptosis by saturated FFA (e.g. stearic acid) but not by unsaturated FFA. Malhi et al. *J. Biol. Chem.* 281:12093-12101 (2006). JNK1−/− mice were not protected from FFA induced injury. The role of JNK1 and JNK2 has been studied in CDAA-fed mice that progressed from steatosis to steatohepatitis to hepatic fibrosis. Kodama et al., *Gastroenterology* 137:1467-1477 (2009). While both JNK1−/− and JNK2−/− mice developed steatosis, the JNK1−/− mice, but not JNK2−/− mice, were remarkably resistant to progression to hepatitis and fibrosis. Chimeric mice with JNK1−/− deletion restricted to bone marrow cells were similarly resistant to hepatitis and fibrosis implicating the activated Kupffer cell as a key trigger for disease progression beyond steatosis. Indeed, JNK1−/− macrophages do not express IL-1, IL-6, TNF and NO in response to LPS, and Kupffer cells derived from JNK1−/− mice or from wild-type mice and treated with JNK inhibitor SP600125 display reduced TNF, IL-6, and IL-1 expression in response to LPS. Sanchez-Tillo et al., *J Biol Chem.* 282(17):12566-73 (2007); Kodama et al., *Gastroenterology* 137:1467-1477 (2009)).

Previous studies have measured levels of IL-10, TNF-α, and NO in cells exposed to UVB irradiation either with or without specific inhibitors, demonstrating that UVB induced the production of those proinflammatory mediators, purportedly via activation of the p38 MAPK signalling pathway. Mutou Y, Tsukimoto M, Homma T, Kojima S, *Immune Response Pathways in Human Keratinocyte (HaCat) Cells are Induced by Ultraviolet B via p38 Mitogen-activated Protein Kinase Activation*, J. Health Science 2010; 56(6): 675-83. Additionally, the induction of c-Jun protein and phosphorylation after UV irradiation of human skin has been reported. Fisher G, Talwar H, Lin J, Lin P, McPhillips F, Wang Z, Li X, Wan Y, Kang S, and Voorhees J, *Retinoic Acid Inhibits Induction of c-Jun Protein by Ultraviolet Radiation That Occurs Subsequent To Activation Of Mitogen-Activated Protein Kinase Pathways In Human Skin In Vivo*, J. Clin Invest. 1998; 101(6): 1432-40 and Einspahr J, Bowden T, Alberts D, McKenzie N, Saboda K, Warneke J, Salasche S, Ranger-Moore J, Lewandrowski C, Nagle R, Nickoloff B, Brooks, C, Dong Z, and Stratton S, *Cross-Validation of*

*Murine UV Signal Transduction Pathaways in Human Skin*, Photochem. Photobiol. 2008; 84(2):463-76.

Clinical markers are needed to evaluate the biological effects of drug candidates. The methods set forth herein allow for the evaluation of the biological effects of JNK inhibitors and, accordingly, are useful in a clinical setting, such as by providing a straight-forward avenue for following the in vivo activity of a JNK inhibitor, and for assessing the sensitivity of a particular patient population to treatment with JNK inhibitors, in particular oral JNK inhibitors.

Citation or identification of any reference in Section 2 of this application is not to be construed as an admission that the reference is prior art to the present application.

3. SUMMARY

Provided herein are methods for evaluating the effect of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof ("Compound 1") in a patient, comprising UVB-irradiation of a patient's skin, administration of Compound 1, and measurement of phosphorylated c-Jun expression in skin using immunohistochemistry. In some embodiments, Compound 1 is administered orally. Also provided herein are methods for evaluating the effect of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof ("Compound 1") in a patient, comprising 1) measuring phosphorylated c-Jun expression in a first skin sample obtained from a first portion of a patient's skin irradiated with UVB-irradiation, 2) measuring phosphorylated c-Jun expression in a second skin sample obtained from a second portion of a patient's skin irradiated with UVB-irradiation after the patient has been administered Compound 1, and 3) comparing the levels of phosphorylated c-Jun in said first skin sample and said second skin sample. The measurement may be carried out in the skin samples using immunohistochemistry. The UVB irradiation may be at 2× minimum erythema dose (MED). The skin in the second skin sample may have been irradiated with UVB irradiation about 2 hours after administration of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof. The skin sample may have been obtained from the portion of skin irradiated with UVB irradiation on the patient's buttock. The second skin sample may have been obtained about 8 hours after the exposure of the skin to UVB irradiation. The measurement of the amount of phosphorylated c-Jun in a skin sample can comprise an immunohistochemical analysis wherein a primary antibody is directed against the phosphorylated c-Jun to form an antibody/phosphorylated c-Jun complex and incubation with a secondary antibody conjugated with a chromogenic enzyme provides a color deposit marking the location of the primary antibody/phoshorylated c-Jun complex in the skin sample. The measurement may further comprise subjective scoring of the color marking or quantitative analysis using a laser scanning cytometer. Compound 1 may be administered orally.

In one embodiment, provided herein are methods for identifying a patient (or patient population) who is sensitive to Compound 1, comprising exposing a first portion of said patient's skin to UVB irradiation, obtaining a sample of said first portion of said patient's skin, measuring the amount of phosphorylated c-Jun in said first portion of said patient's skin, administering an effective amount of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin indicates that said patient is sensitive to Compound 1. Also provided herein are methods for identifying a patient (or patient population) who is sensitive to Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered Compound 1, and 3) comparing the levels of phosphorylated c-Jun in said first skin sample and said second skin sample, wherein a decrease in the level of phosphorylated c-Jun in said second skin sample to said first skin sample indicates that said patient is sensitive to Compound 1. The decrease in the level can be at least about 5%, about 10%, about 15%, about 20%, about 25%, about 30%, about 35%, about 40%, about 45%, about 50% or more.

In another embodiment, provided herein are methods for evaluating the effect of Compound 1 in a patient, comprising UVB-irradiation of a patient's skin, administration of Compound 1, and measurement of phosphorylated c-Jun expression in skin using immunohistochemistry. Also provided herein are methods for evaluating the effect of Compound 1 in a patient, wherein the method comprises measuring phosphorylated c-Jun expression using immunohistochemistry in skin samples irradiated with UVB irradiation after the patient has been administered Compound 1.

In another embodiment, provided herein are methods for evaluating inhibition of JNK in a patient by measuring phosphorylated c-Jun in the patient's skin. In one embodiment, provided herein are methods of measuring inhibition of JNK in a patient by exposing a first portion of said patient's skin to UVB irradiation, obtaining a sample of said first portion of said patient's skin, measuring the amount of phosphorylated c-Jun in said first portion of said patient's skin, administering Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a decreased level of phosphorylated c-Jun in said second portion of said patient's skin relative to said first portion of said patient's skin indicates inhibition of JNK.

In another embodiment, methods for determining a dose-response relationship for the administration of Compound 1 in a patient are provided. The methods comprise administering to said patient varying doses (e.g., from about 1 mg to 1000 mg) of Compound 1 and determining the amount of JNK inhibition in said patient resulting from each dose of Compound 1, comprising exposing a first portion of said patient's skin to UVB irradiation, obtaining a sample of said first portion of said patient's skin, measuring the amount of phosphorylated c-Jun in said first portion of said patient's skin, administering a dose of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin is proportional to the inhibition of JNK. Also provided herein is a method for determining a dose-response relationship for the administration of Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered varying doses of Compound 1 (e.g., from about 1 mg to 1000 mg), and 3) comparing the levels of phosphorylated c-Jun in said first skin sample and said second skin sample, wherein a decrease in the level of phosphorylated c-Jun in said second skin sample to said first skin sample is proportional to the inhibition of JNK. The decrease in the level may be at least about 5%, about 10%, about 15%, about 20%, about 25%, about 30%, about 35%, about 40%, about 45%, about 50% or more.

In other embodiments, methods for determining the effective amount of Compound 1 for the treatment or management of a disease or condition associated with JNK in a patient are provided, which comprise administering to said patient varying doses (e.g., from about 1 mg to 1000 mg) of Compound 1 and determining the amount of JNK inhibition in said patient resulting from each dose of Compound 1, comprising exposing a first portion of said patient's skin to UVB irradiation, obtaining a sample of said first portion of said patient's skin, measuring the amount of phosphorylated c-Jun in said first portion of said patient's skin, administering a dose of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a 50% decrease in the level of phosphorylated c-Jun in said second portion of said patient's skin relative to said first portion of said patient's skin is indicative of the administration of an effective amount of Compound 1. Also provided herein is a method for determining an effective amount of Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered varying doses of Compound 1 (e.g., from about 1 mg to 1000 mg), and 3) comparing the levels of phosphorylated c-Jun in said first skin sample and said second skin sample, wherein a 50% decrease in the level of phosphorylated c-Jun in said second skin sample to said first skin sample is indicative of the administration of an effective amount of Compound 1.

In yet another embodiment, a method for monitoring patient compliance with Compound 1 therapy is provided. The method comprises measuring the level of phosphorylated c-Jun or c-Jun expressed in a sample of the patient's skin and determining if the expression level is increased or decreased in the sample of the patient's skin compared to the expression level in a control untreated sample, wherein decreased expression indicates patient compliance with the Compound 1 therapy.

The JNK inhibitor useful in the methods provided herein is:

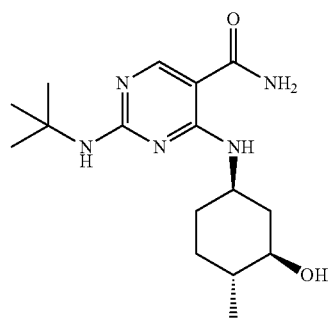

having the alternative names 2-(tert-butylamino)-4-((1R,3R,4R)-3-hydroxy-4-methylcyclohexylamino)-pyrimidine-5-carboxamide or 2-[(1,1-dimethylethyl)amino]-4-[[(1R,3R,4R)-3-hydroxy-4-methylcyclohexyl]amino]-5-pyrimidinecarboxamide or a pharmaceutically acceptable stereoisomer, tautomer, solid form, polymorph, salt, hydrate, clathrate, or solvate thereof (collectively referred to herein as "Compound 1"). Compound 1 is disclosed in U.S. Patent Application Publication No. 2013/0029987, published on Jan. 31, 2013, and International Pub. No. WO2012/145569, the entireties of each of which are incorporated by reference herein.

4. BRIEF DESCRIPTION OF THE DRAWINGS

5. DETAILED DESCRIPTION

5.1. Definitions

Figure 1:
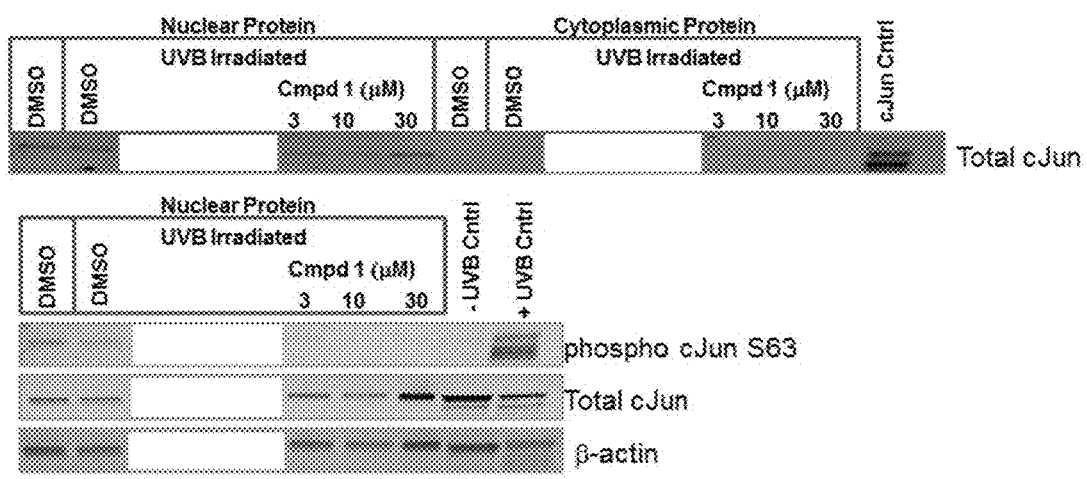
FIG. 1 depicts activation of c-Jun at Ser63 with 50 mJ/cm$^2$ UVB radiation and inhibition with Compound 1 in Donor 1 HEka cells (as determined by Western immunoblotting).
Figure 2:
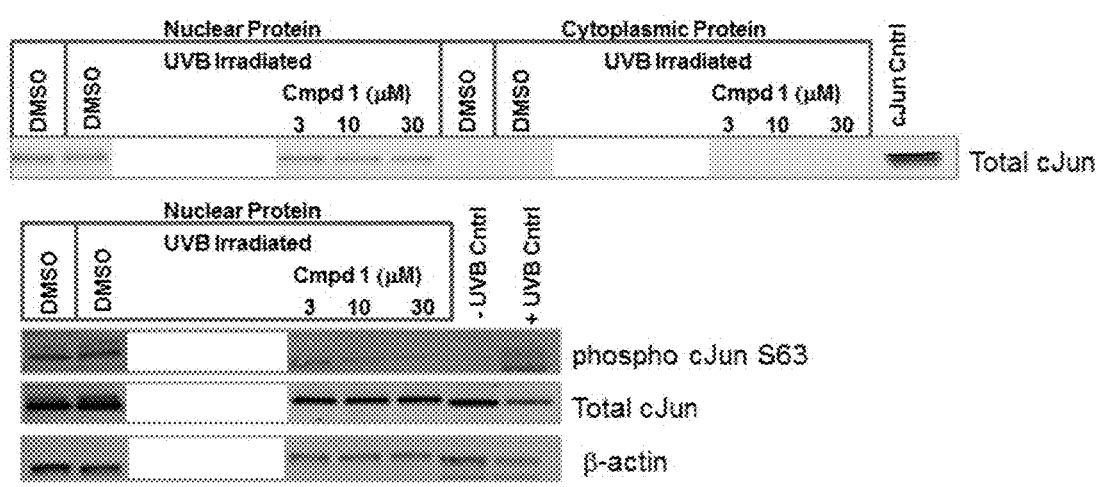
FIG. 2 depicts activation of c-Jun at Ser63 with 50 mJ/cm$^2$ UVB radiation and inhibition with Compound 1 in Donor 2 HEka cells (as determined by Western immunoblotting).
Figure 3:
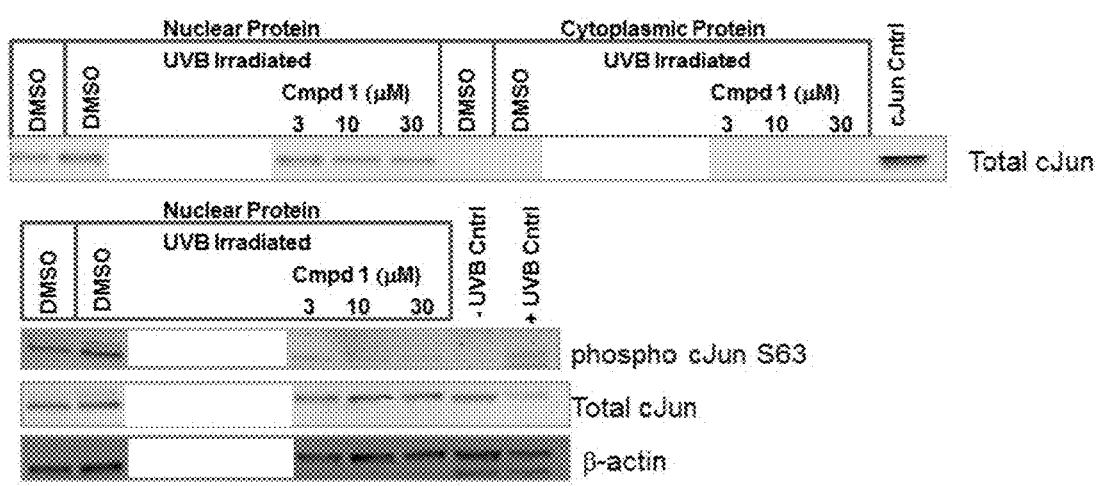
FIG. 3 depicts activation of c-Jun at Ser63 with 50 mJ/cm$^2$ UVB radiation and inhibition with Compound 1 in Donor 3 HEka cells (as determined by Western immunoblotting).
Figure 4:
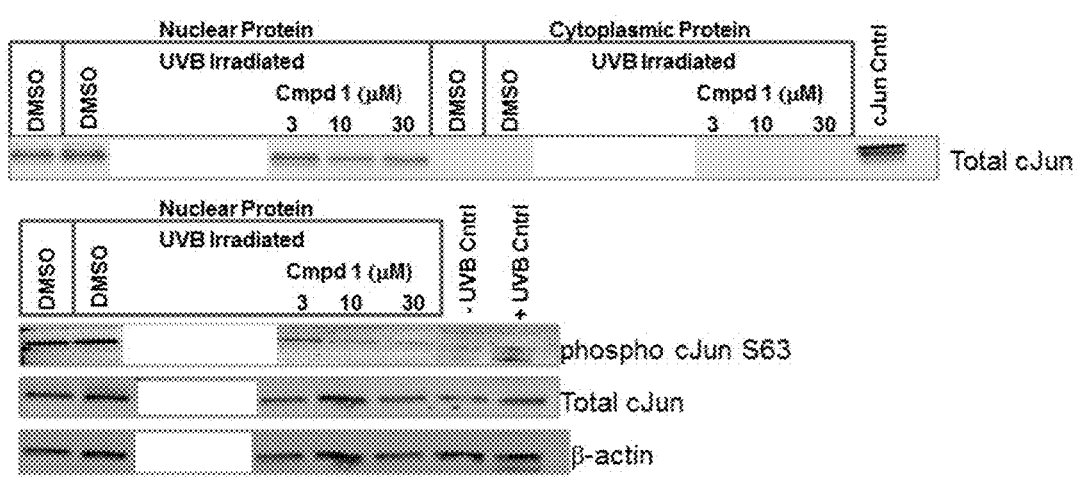
FIG. 4 depicts activation of c-Jun at Ser63 with 50 mJ/cm$^2$ UVB radiation and inhibition with Compound 1 in Donor 4 HEka cells (as determined by Western immunoblotting).

The term "JNK" means a protein or an isoform thereof expressed by a JNK 1, JNK 2, or JNK 3 gene (Gupta, S., Barrett, T., Whitmarsh, A. J., Cavanagh, J., Sluss, H. K., Derijard, B. and Davis, R. J. *The EMBO J.* 15:2760-2770 (1996)).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, L-asparate, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "stereoisomer" or "stereomerically pure" means one stereoisomer of a compound of formula (I) that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds of formula (I) can have chiral centers and can occur as racemates, individual enantiomers or diastereomers, and mixtures thereof. All such isomeric forms are included within the embodiments disclosed herein, including mixtures thereof.

The use of stereomerically pure forms of such compounds of formula (I), as well as the use of mixtures of those forms, are encompassed by the embodiments disclosed herein. For example, mixtures comprising equal or unequal amounts of the enantiomers of a particular compound of formula (I) may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds of formula (I) can include E and Z isomers, or a mixture thereof, and cis and trans isomers or a mixture thereof. In certain embodiments, the compounds of formula (I) are isolated as either the E or Z isomer. In other embodiments, the compounds of formula (I) are a mixture of the E and Z isomers.

The term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

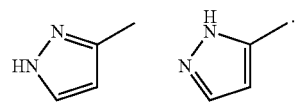

Compound 1 contains one or more chiral centers, and can exist as racemic mixtures of enantiomers, mixtures of diastereomers or enantiomerically or optically pure compounds. The use of stereomerically pure forms of such compounds, as well as the use of mixtures of those forms are encompassed by the embodiments disclosed herein. As a non-limiting example, mixtures comprising equal or unequal amounts of the enantiomers of Compound 1 may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

The term "treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g. viral infection such as HCV), with liver transplant, or with drug induced liver injury (e.g. acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e. fatty liver), hepatitis or cirrhosis, or a slowing, or halting of further progression or worsening of those symptoms. In one embodiment, the symptom is jaundice. In another embodiment, "treating" means and alleviation, in whole or in part, of a disorder, disease or condition, or symptoms associated with a condition, treatable or preventable by inhibition of a JNK pathway.

The term "preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a liver fibrotic disorder, or diabetes or metabolic syndrome leading to liver fibrotic disorders, as described herein, or symptoms thereof. In one embodiment, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g. viral infection such as HCV), with liver transplant, or with drug induced liver injury (e.g. acetaminophen toxicity). In another, the disorder is a condition, treatable or preventable by inhibition of a JNK pathway.

The terms "sensitivity" and "sensitive" when made in reference to treatment is a relative term which refers to the degree of effectiveness of Compound 1 in lessening or decreasing the symptoms of the disease being treated. For example, the term "increased sensitivity" when used in reference to treatment of a cell or patient refers to an increase of, at least a 5%, or more, in the effectiveness in lessening or decreasing the symptoms of a disease or condition associated with JNK when measured using any methods well-accepted in the art or as disclosed herein.

The term "effective amount" in connection with Compound 1 means an amount capable of treating or preventing a disorder, disease or condition, or symptoms thereof, disclosed herein.

As used herein "UVB" refers to electro-magnetic radiation that is in the region of the ultraviolet spectrum which extends from about 280 nm to about 320 nm.

The term "likelihood" generally refers to an increase in the probability of an event. The term "likelihood" when used in reference to the effectiveness of a patient response generally contemplates an increased probability that the symptoms of a disease or condition associated with JNK will be lessened or decreased.

The term "predict" generally means to determine or tell in advance. When used to "predict" the effectiveness of Compound 1 treatment, for example, the term "predict" can mean that the likelihood of the outcome of the treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the efficacy of a treatment for a disease or condition associated with JNK" refers to tracking the effectiveness in treating a patient. Similarly, the term "monitoring," when used in connection with patient compliance, either individually, or in a clinical trial, refers to the tracking or confirming that the patient is actually following the treatment regimen being tested as prescribed.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for having interstitial pulmonary fibrosis, systemic sclerosis, scleroderma, chronic allograft nephropathy, antibody mediated rejection, or lupus. In another, a subject is a human having or at risk for having liver fibrotic disorders or diabetes or metabolic syndrome leading to liver fibrotic disorders, or a condition, treatable or preventable by inhibition of a JNK pathway, or a symptom thereof. In one embodiment, a subject is fasted. In another embodiment, a subject is fed.

5.2. Use of c-Jun N-Terminal Kinases as Biomarkers

Methods provided herein are based, in part, on the discovery that the presence and level of phosphorylated c-Jun or c-Jun in patient skin samples can be utilized as a biomarker to follow the inhibition of JNK. In particular, these biomarkers can be used to predict, assess, and track the effectiveness of Compound 1 therapy in a patient, in particular oral therapy with Compound 1, or to monitor the patient's compliance to the prescribed regimen of Compound 1 therapy.

The baseline phosphorylated c-Jun immune-reactivity in healthy human skin is low without UVB exposure. UVB-irradiation reliably increases levels of phosphorylated c-Jun, as reflected by an increase in phosphorylated c-Jun immunoreactivity in tissue sections. The increase starts to plateau at approximately 8 hours post UVB exposure. The inhibition of JNK is dose-related. UVB-irradiation induced increases in phosphorylated c-Jun can be used as a model to evaluate Compound 1, including the evaluation of dose-response, and to identify patient populations who are sensitive to Compound 1.

Provided herein are methods relating to the use of phosphorylated c-Jun levels induced by UVB-irradiation as a biomarker to evaluate the effectiveness of Compound 1. Phosphorylated c-Jun and c-Jun levels can be used to determine whether a treatment is likely to be successful in diseases or conditions associated with JNK.

In certain embodiments, the methods provided herein allow for the amount of in vivo inhibition of JNK resulting from administration of Compound 1 to be determined. In certain embodiments, the assays provided herein comprise exposing a first portion of said patient's skin to UVB irradiation, obtaining a sample of said first portion of said patient's skin, measuring the amount of phosphorylated c-Jun or c-Jun in said first portion of said patient's skin immunohistochemically, administering Compound 1 to said patient, exposing a second portion of said patient's skin to UVB irradiation, obtaining a sample of said second portion of said patient's skin, measuring the amount of phosphorylated c-Jun or c-Jun in said second portion of said patient's skin immunohistochemically, and comparing the levels of phosphorylated c-Jun or c-Jun in said first portion of said patient's skin and said second portion of said patient's skin, wherein a reduction of levels of phosphorylated c-Jun or c-Jun in said second portion of said patient's skin compared to said first portion of said patient's skin indicates inhibition of JNK. Also provided herein is a method for evaluating inhibition of JNK in a patient comprising: 1) measuring the amount of phosphorylated c-Jun or c-Jun in a first skin sample obtained from a first portion of a patient's skin irradiated with UVB irradiation, 2) measuring the amount of phosphorylated c-Jun or c-Jun in a second skin sample obtained from a second portion of a patient's skin irradiated with UVB irradiation after said patient has been administered Compound 1, and 3) comparing the levels of phosphorylated c-Jun in said first skin sample and said second skin sample, wherein a reduction of levels of phosphorylated c-Jun or c-Jun in said second skin sample to said first skin sample indicates inhibition of JNK. In some embodiments the reduction is at least about 5%, about 10%, about 15%, about 20%, about 25%, about 30%, about 35%, about 40%, about 45%, about 50% or more. In certain embodiments, the assays provided herein comprise using human skin model tissues. In such embodiments, the assays comprise exposing a first sample of said tissue to UVB irradiation, obtaining a sample of said first portion of said tissue, measuring the amount of phosphorylated c-Jun or c-Jun in said first portion of said tissue immunohistochemically, administering Compound 1 to said tissue, exposing a second portion of said tissue to UVB irradiation, obtaining a sample of said second portion of said tissue, measuring the amount of phosphorylated c-Jun or c-Jun in said second portion of said tissue immunohistochemically, and comparing the levels of phosphorylated c-Jun or c-Jun in said first portion of said tissue and said second portion of said tissue, wherein a reduction of levels of phosphorylated c-Jun or c-Jun in said second portion of said tissue compared to said first portion of said tissue indicates inhibition of JNK. In some embodiments the reduction is at least about 5%, about 10%, about 15%, about 20%, about 25%, about 30%, about 35%, about 40%, about 45%, about 50% or more.

In such embodiments, human skin model tissues such as EpiDermFT may be used. EpiDermFT is a reconstituted human skin equivalent, which exhibits morphological and growth characteristics similar to human skin, and has been used widely as a model tissue system in studies relevant to human skin (see, e.g., Zhao J F, Zhang Y J, Kubilus J, Jin X H, Santella R M, Athar M, Wang Z Y, Bickers D R. *Reconstituted 3-Dimensional Human Skin as a Novel in Vitro Model for Studies of Carcinogen*, Biochemical and Biophysical Research Comms. 1999; 254:49-53; Mahns A, Wolber R, Stab F, Klotz L O, Sies H, *Contribution of UVB and UVA to UV-dependent stimulation of cyclooxygenase-2 expression in articfical epidermis*, Photochem. Photobiol. Sci. 2004; 3:257-62; Sedelnikova O A, Nakamura A, Kovalchuk O, Koturbash I, Mitchell S A, Marino S A, Brenner D J, Bonner W M, *DNA Double-Strand Breaks Form in Bystander Cells after Microbeam Irradiation of Three-dimensional Human Tissue Models*, Cancer Res 2007; 67(9): 4295-4302; Hayden P J, Burnham B, Klausner M, Kubilus J, Sheasgreen J E, *Wound Healing Response of the EpiDerm Full Thickness (EpiDerm-FT) In Vitro Human Skin Equivalent after Solar UV Irradiation*, Presented at the 5$^{th}$ World Congress, Berlin, Germany, August 2005 & The Society of Investigative Dermatology Meeting, Providence, R.I., April-May 2004, TR-328:1-10). EpiDermFT samples may be obtained from MatTek Corporation (Ashland, Mass.).

In some embodiments, the immunohistochemistry evaluations of the skin biopsies provided by the methods herein to assess JNK activation comprise a two antibody IHC assay that employs a primary antibody, directed against the target phosphorylated c-Jun or c-Jun, and a secondary antibody conjugated with a chromogenic enzyme. In such embodiments, the secondary antibody-reporter conjugate deposits a red color when incubated with the substrate reaction mixture, thus marking the location of the primary antibody target complex. This red color is then recorded with standard bright-field illumination using, e.g., a Nikon microscope. The microscope images are then photographed and electronic images may be scored (blinded) by independent and trained scorers using guidelines as illustrated in the Examples. In certain embodiments, exploratory quantitative IHC analysis may be carried out using a laser scanning cytometer. In such embodiments, the slides are further processed in order to define the nuclear compartment of the epithelial keratinocytes. In such embodiments, the same IHC slides are counterstained with Hematoxylin to tag the nuclear compartment, then scanned using two photodiode channels, 488 nm for the DAB stain (to mark the primary antibody directed against phosphorylated c-Jun or c-Jun) and 633 nm for the Hematoxylin stain, then the nuclei are counted based upon the Hematoxylin signal and then the DAB signals are integrated for each nucleus in the epithelium.

In some embodiments, the methods provided herein allow for the measurement of phosphorylated c-Jun or c-Jun levels, before and after administration of Compound 1, which can be used as biomarkers for measuring the inhibition of JNK by Compound 1 in a patient.

In some embodiments of the methods provided herein, a decreased level of phosphorylated c-Jun or c-Jun in said second portion of said patient's skin relative to said first portion of said patient's skin indicates inhibition of JNK by Compound 1.

In some embodiments of the methods provided herein, a decreased level of phosphorylated c-Jun or c-Jun in said second portion of said patient's skin relative to said first portion of said patient's skin is proportional to the inhibition of JNK by Compound 1.

In some embodiments, the methods provided herein allow for the measurement of phosphorylated c-Jun or c-Jun levels before and after administration of Compound 1, which can be used as biomarkers for determining whether a patient is sensitive to Compound 1.

In some embodiments of the methods provided herein, a decreased level of phosphorylated c-Jun or c-Jun in said second portion of said patient's skin relative to said first portion of said patient's skin indicates that said patient is sensitive to Compound 1.

In some embodiments, the methods provided herein allow for the measurement of phosphorylated c-Jun or c-Jun levels before and after administration of Compound 1, which can be used to determine the effective amount of Compound 1 for the treatment or prevention of a disease or condition associated with JNK in a patient.

In some embodiments of the methods provided herein, a decreased level of phosphorylated c-Jun or c-Jun in said second portion of said patient's skin relative to said first portion of said patient's skin may be correlated to indicate the administration of an effective amount of Compound 1.

5.3. Compound 1

The JNK inhibitor useful in the methods provided herein is:

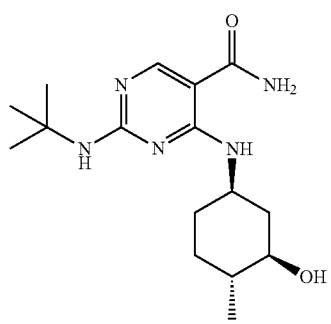

having the alternative names 2-(tert-butylamino)-4-((1R,3R,4R)-3-hydroxy-4-methylcyclohexylamino)-pyrimidine-5-carboxamide or 2-[(1,1-dimethylethyl)amino]-4-[[(1R,3R,4R)-3-hydroxy-4-methylcyclohexyl]amino]-5-pyrimidinecarboxamide or a pharmaceutically acceptable stereoisomer, tautomer, solid form, polymorph, salt, hydrate, clathrate, or solvate thereof ("collectively referred to herein as "Compound 1"). Compound 1 is disclosed in U.S. Patent Application Publication No. 2013/0029987, published on Jan. 31, 2013, and International Pub. No. WO2012/145569, the entireties of each of which are incorporated by reference herein.

In one embodiment, Compound 1 is a free base. In certain embodiments, the free base is a solid. In certain embodiments, the free base is an amorphous solid. In yet another embodiment, the free base is crystalline.

In another embodiment, Compound 1 is a pharmaceutically acceptable solvate of the free base. In one embodiment, the solvate is a hydrate. In another embodiment, the hydrate is in a crystalline form.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.4. Methods for Making Compound 1

Compound 1 can be made using conventional organic syntheses using reagents and methods known in the art, including the methods provided in U.S. Patent Application Publication No. 2013/0029987, published on Jan. 31, 2013, U.S. Provisional Patent Application No. 61/933,636, filed on Jan. 30, 2014, U.S. Provisional Patent Application No. 62/025,161, filed on Jul. 16, 2014, and International Pub. No. WO2012/145569, the entire contents of each of which are incorporated herein by reference.

5.5. Methods of Administration and Dosage

Compound 1 can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of Compound 1 in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of Compound 1 to be administered to a subject is rather widely variable and can be subject to the judgment of a health-care practitioner. In general, Compound 1 can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of Compound 1 administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of Compound 1 to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day, about 60 mg/day to about 720 mg/day, about 240 mg/day to about 720 mg/day or about 600 mg/day to about 800 mg/day of Compound 1 to a subject in need thereof.

In another embodiment, provided herein are methods for the treatment or prevention of a disease or disorder comprising the administration of Compound 1. In yet another embodiment, provided herein are methods for the treatment and prevention of a disease or disorder comprising administration of about 10 mg/day, about 30 mg/day, about 60 mg/day, about 120 mg/day, about 160 mg/day, about 200 mg/day, about 240 mg/day, about 400 mg/day, about 480 mg/day, or about 720 mg/day per day of Compound 1. In a particular embodiment, the methods disclosed herein comprise the administration of about 400 mg/day, about 600 mg/day or about 800 mg/day of Compound 1 to a subject in need thereof. In a particular embodiment, the methods disclosed herein comprise the administration of about 60 mg/day, about 160 mg/day or about 400 mg/day of Compound 1 to a subject in need thereof.

In another embodiment, provided herein are methods for the treatment or prevention of a disease or disorder comprising the administration of about 10 mg/day to about 720 mg/day, about 10 mg/day to about 480 mg/day, about 60 mg/day to about 720 mg/day or about 240 mg/day to about 720 mg/day of Compound 1 to a subject in need thereof.

In one embodiment, provided herein are methods for the treatment or prevention of a disease or disorder comprising the administration of about 10 mg/day, about 30 mg/day, about 60 mg/day, about 120 mg/day, about 240 mg/day, about 480 mg/day, or about 720 mg/day of Compound 1 to a subject in need thereof. In one embodiment, provided herein are methods for the treatment or prevention of a disease or disorder comprising the administration of about 60 mg/day, about 160 mg/day, or about 400 mg/day of Compound 1 to a subject in need thereof. In another embodiment, provided herein are methods for the treatment or prevention of a disease or disorder comprising the administration about 200 mg/day of Compound 1 to a subject in need thereof. In one embodiment, provided herein are methods for the treatment or prevention of a disease or disorder comprising the administration of about 10 mg/day, about 30 mg/day, about 60 mg/day, about 120 mg/day, about 160 mg/day, about 200 mg/day, about 240 mg/day, about 400 mg/day, about 480 mg/day, or about 720 mg/day of Compound 1 to a subject in need thereof.

In another embodiment, provided herein are unit dosage formulations that comprise between about 10 mg and about 100 mg, about 1 mg and about 200 mg, about 30 mg and about 200 mg, about 35 mg and about 1400 mg, about 125 mg and about 1000 mg, about 250 mg and about 1000 mg, or about 500 mg and about 1000 mg of Compound 1.

In another embodiment, provided herein are unit dosage formulations that comprise about 1 mg, about 5 mg, about 10 mg, about 15 mg, about 20 mg, about 30 mg, about 35 mg, about 50 mg, about 60 mg, about 70 mg, about 100 mg, about 120 mg, about 125 mg, about 140 mg, about 175 mg, about 200 mg, about 240 mg, about 250 mg, about 280 mg, about 350 mg, about 480 mg, about 500 mg, about 560 mg, about 700 mg, about 720 mg, about 750 mg, about 1000 mg or about 1400 mg of Compound 1.

In another embodiment, provided herein are unit dosage forms that comprise about 30 mg, about 100 mg or about 200 mg of Compound 1.

Pharmaceutical compositions, and dosage forms of Compound 1 can be administered once, twice, three, four or more times daily. In one embodiment, pharmaceutical compositions, and dosage forms of Compound 1 can be administered once daily for 14 days.

Compound 1 can be administered orally for reasons of convenience. In one embodiment, when administered orally, Compound A is administered with a meal and water. In another embodiment, Compound 1 (e.g., granules or dispersible tablets) is dispersed in water or juice (e.g., apple juice or orange juice) and administered orally as a suspension.

Compound 1 can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing Compound 1 without an additional carrier, excipient or vehicle.

In another embodiment, provided herein are compositions comprising an effective amount of Compound 1 and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing Compound 1 with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer Compound 1 as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of Compound 1 can be delayed or prolonged by proper formulation. For example, a slowly soluble pellet of Compound 1 can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending Compound 1 in oily or emulsified vehicles that allow it to disperse slowly in the serum.

5.6. Methods of Use

Provided herein are methods for the use of UVB-irradiation of skin and measurement of phosphorylated c-Jun using immunohistochemistry as a model to determine the effect of Compound 1 in human and other patients. The methods provided herein can accelerate the clinical development of Compound 1 as the model shows whether the compound at issue hits the JNK target in a patient and also allows the evaluation of dose-response in a patient; which guides the dose selection in clinical development.

The baseline phosphorylated c-Jun immune-reactivity in healthy human skin is low without UVB exposure. UVB-irradiation reliably increases phosphorylated c-Jun immunoreactivity. The increase starts to plateau at approximately 8 hours post UVB exposure. The inhibition of JNK is dose-related. Thus, UVB-irradiation and phosphorylated c-Jun can be used as a model to evaluate Compound 1, including the evaluation of dose-response, and to identify patient populations who are sensitive to Compound 1.

In one embodiment, provided herein are methods for identifying a patient (or patient population) who is sensitive to Compound 1, comprising exposing a first portion of said patient's skin to UVB irradiation, obtaining a sample of said first portion of said patient's skin, measuring the amount of phosphorylated c-Jun in said first portion of said patient's skin, administering an effective amount of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin indicates that said patient is sensitive to Compound 1. In certain embodiments, the methods further comprise the treatment or prevention of a disease provided herein by administration of an amount of Compound 1 effective for treatment or prevention of the disease. Also provided herein is a method for identifying a patient who is sensitive to Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered Compound 1, and 3) comparing the levels of phosphorylated c-Jun in said first skin sample and said second skin sample, wherein a decrease in the level of phosphorylated c-Jun in said second skin sample to said first skin sample indicates that said patient is sensitive to Compound 1. Also provided herein is Compound 1 for use in a method for treating or preventing a disease as disclosed herein, wherein the method comprises said method for identifying a patient who is sensitive to Compound 1.

In certain embodiments, provided herein are methods for evaluating the effect of Compound 1 in a patient, comprising UVB-irradiation of a patient's skin, administration of Compound 1, and measurement of phosphorylated c-Jun expression in skin using immunohistochemistry. Also provided herein are methods for evaluating the effect of Compound 1 in a patient, wherein the method comprises measuring phosphorylated c-Jun expression using immunohistochemistry in skin samples irradiated with UVB irradiation after the patient has been administered Compound 1. In one embodiment, Compound 1 is administered in combination with an inhibitor(s) of MAP kinase. In one embodiment, the effect of Compound 1 is the dose-response relationship of Compound 1 in a patient. In some embodiments, Compound 1 is administered orally. In certain embodiments, the methods further comprise the treatment or prevention of a disease provided herein by administration of an amount of Compound 1 effective for treatment of prevention of the disease. Also provided herein is Compound 1 for use in a method for treating or preventing a disease as disclosed herein, wherein the method comprises said method for evaluating the effect of Compound 1 in a patient.

Further provided herein are methods for evaluating inhibition of JNK in a patient by measuring phosphorylated c-Jun in the patient's skin. In one embodiment, provided herein are methods of measuring inhibition of JNK in a patient by exposing a first portion of said patient's skin to UVB irradiation, obtaining a sample of said first portion of said patient's skin, measuring the amount of phosphorylated c-Jun in said first portion of said patient's skin, administering Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a decreased level of phosphorylated c-Jun in said second portion of said patient's skin relative to said first portion of said patient's skin indicates inhibition of JNK. In certain embodiments, the method further comprises the treatment or prevention of a disease provided herein by administration of an amount of Compound 1 effective for treatment of prevention of the disease. Also provided herein is a method for evaluating inhibition of JNK in a patient comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered Compound 1, and 3) comparing the levels of phosphorylated c-Jun in said first skin sample and said second skin sample, wherein a decrease in the level of phosphorylated c-Jun in said second skin sample to said first skin sample indicates inhibition of JNK. Also provided herein is Compound 1 for use in a method for treating or preventing a disease as disclosed herein, wherein the method comprises said method for evaluating inhibition of JNK in a patient.

In another embodiment, methods for determining a dose-response relationship for the administration of Compound 1 in a patient are provided. The methods comprise administering to said patient varying doses (e.g., from about 1 mg to 1000 mg) of Compound 1 and determining the amount of JNK inhibition in said patient resulting from each dose of Compound 1, comprising exposing a first portion of said patient's skin to UVB irradiation, obtaining a sample of said first portion of said patient's skin, measuring the amount of phosphorylated c-Jun in said first portion of said patient's skin, administering a dose of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin is proportional to the inhibition of JNK. In certain embodiments, the method further comprise the treatment or prevention of a disease provided herein by administration of an amount of Compound 1 effective for treatment of prevention of the disease. Also provided herein is a method for determining a dose-response relationship for the administration of Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered a dose of Compound 1, and 3) comparing the levels of phosphorylated c-Jun in said first skin sample and said second skin sample, wherein a decrease in the level of phosphorylated c-Jun in said second skin sample to said first skin sample is proportional to the inhibition of JNK. Also provided herein is Compound 1 for use in a method for treating or preventing a disease as disclosed herein, wherein the method comprises said method for determining a dose-response relationship for the administration of Compound 1.

In other embodiments, methods for determining the effective amount of Compound 1 for the treatment or management of a disease or condition associated with JNK in a patient are provided, which comprise administering to said patient varying doses (e.g., from about 1 mg to 1000 mg) of Compound 1 and determining the amount of JNK inhibition in said patient resulting from each dose of Compound 1, comprising exposing a first portion of said patient's skin to UVB irradiation, obtaining a sample of said first portion of said patient's skin, measuring the amount of phosphorylated c-Jun in said first portion of said patient's skin, administering a dose of Compound 1 to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a 50% decrease in the level of phosphorylated c-Jun in said second portion of said patient's skin relative to said first portion of said patient's skin is indicative of the administration of an effective amount of Compound 1. In certain embodiments, the method further comprise the treatment or prevention of a disease provided herein by administration of an amount of Compound 1 effective for treatment of prevention of the disease. Also provided herein is a method for determining an effective amount of Compound 1, comprising: 1) measuring the amount of phosphorylated c-Jun in a first skin sample obtained from a first portion of a patient's skin irradiated with UVB irradiation, 2) measuring the amount of phosphorylated c-Jun in a second skin sample obtained from a second portion of a patient's skin irradiated with UVB irradiation after said patient has been administered a dose of Compound 1, and 3) comparing the levels of phosphorylated c-Jun in said first skin sample and said second skin sample, wherein a 50% decrease in the level of phosphorylated c-Jun in said second skin sample to said first skin sample is indicative of the administration of an effective amount of Compound 1. Also provided herein is Compound 1 for use in a method for treating or preventing a disease as disclosed herein, wherein the method comprises said method for determining an effective amount of Compound 1.

In yet another embodiment, a method for monitoring patient compliance with Compound 1 therapy is provided. The method comprises measuring the level of phosphorylated c-Jun or c-Jun expressed in a sample of the patient's skin and determining if the expression level is increased or decreased in the sample of the patient's skin compared to the expression level in a control untreated sample, wherein decreased expression indicates patient compliance with Compound 1 therapy. In certain embodiments, the method further comprise the treatment or prevention of a disease provided herein by administration of an amount of Compound 1 effective for treatment of prevention of the disease.

In another embodiment, provided herein are methods for treating a patient (or patient population) comprising the administration of Compound 1 to the patient (or patient population), wherein the patient (or patient population) has been determined to have a likelihood of response or has been determined to be sensitive to Compound 1.

Diseases treatable or preventable by the methods provided herein include liver fibrotic disorders, such as non-alcoholic steatohepatitis, steatosis (i.e. fatty liver), cirrhosis, primary sclerosing cholangitis, primary biliary cirrhosis, hepatitis, hepatocellular carcinoma, and liver fibrosis coincident with chronic or repeated alcohol ingestion (alcoholic hepatitis), with infection (e.g. viral infection such as HCV), with liver transplant, or with drug induced liver injury (e.g. acetaminophen toxicity). In some such aspects, diseases treatable or preventable by the methods provided herein include diabetes or metabolic syndrome leading to liver fibrotic disorders, such as non-alcoholic steatohepatitis, steatosis (i.e. fatty liver), cirrhosis, primary sclerosing cholangitis, primary biliary cirrhosis, and hepatitis.

In another aspect, diseases treatable or preventable by the methods provided herein include interstitial pulmonary fibrosis, systemic sclerosis, scleroderma, chronic allograft nephropathy, antibody mediated rejection, or lupus. In some such embodiments, the lupus is lupus erythematosus (such as discoid lupus erythematosus, or cutaneous lupus erythematosus) or systemic lupus.

In another aspect, diseases or conditions treatable or preventable by the methods provided herein include those treatable or preventable by inhibition of JNK1 and/or JNK2. Examples of such conditions include rheumatoid arthritis; rheumatoid spondylitis; osteoarthritis; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

6. EXAMPLES

The examples below are carried out using standard techniques, except where otherwise described in detail. The examples are intended merely to be illustrative.

6.1. Methods for UV Irradiation

Figure 5:
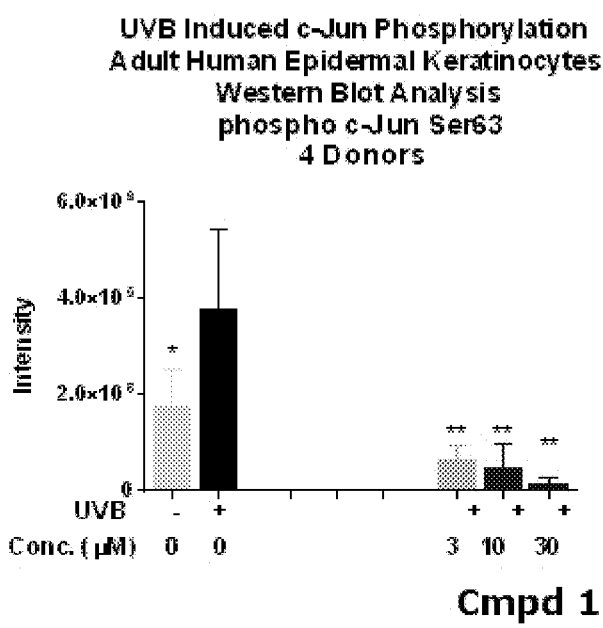
FIG. 5 depicts inhibition of phosphorylation of c-Jun at Ser63 induced by 50 mJ/cm$^2$ UVB radiation in HEka cells.

Adult Normal Human Neonatal Keratinocytes (HEKa) were obtained from ScienCell. Cells were plated in 10 cm dishes and incubated to allow attachment and then serum starved overnight. Compound 1 was added 1 hour before the cells were irradiated with 50 mJ/cm$^2$ UVB. Cells were incubated with Compound 1 for an additional 30 minutes after UVB irradiation. Cells were then lysed and nuclear and cytoplasmic proteins were isolated using the Nuclear Extraction kit by Active Motif. Protein was run on 10% tris glycine gels and transferred to nitrocellulose membranes. Blots were blocked for 1 hour. Total and phosphorylated c-Jun primary antibodies were added and incubated overnight. Licor secondary antibodies were added and blots were read on the Li-Cor Odyssey. Results for HEKa cells from four donors are set forth in Figures. 1-5. There was increased phosphorylation of c-Jun at Ser63 with 50 mJ/cm$^2$ UVB radiation, and inhibition by Compound 1 (FIGS. 1-5). There was also good separation of the nuclear and cytoplasmic proteins (c-Jun is only in the nucleus) (FIGS. 1-4). Compound 1 inhibits c-Jun phosphorylation at Ser63 in a dose dependent manor (FIG. 5).

6.2. Clinical Protocol

A Two-Part, Phase 1 Study to Evaluate the Pharmacokinetics and Pharmacodynamics of Multiple Dose Compound 1 and the Effects of Food and Formulation on the Pharmacokinetics of Single Dose Compound 1 in Healthy Subjects Primary Objectives:
Part 1: To evaluate the effect of multiple oral doses of Compound 1 on JNK activity following ultraviolet (UV) irradiation of human skin
Part 2: To evaluate pharmacokinetics of formulated Compound 1 tablets in the presence of food, and the relative bioavailability of formulated Compound 1 tablets compared to the active-ingredient-in capsule (AIC) formulation following a single oral dose.

Secondary Objectives:
Part 1: To evaluate the safety of single and multiple oral doses of Compound 1.
Part 2: To evaluate the safety and tolerability of formulated Compound 1 tablets when administered with food.

Study Design:
This is a two-part, Phase 1 study to evaluate the pharmacokinetics and pharmacodynamics of multiple doses of Compound 1 and the effects of food and formulation on the pharmacokinetics of single dose Compound 1 in healthy subjects.

Part 1:
This is an open-label, multiple-dose, 3-period, fixed sequence study, to evaluate the effect of Compound 1 on JNK activity following UV irradiation.

The study will consist of a screening phase (Day −21 to −2), minimum erythema dose (MED) determination prior to dosing, baseline (Day −1), 3 treatment/assessment periods during which increasing doses of Compound 1 are administered, and a follow-up visit. There will be no washout in between periods.

On the first day prior to dosing (baseline), and on the 6$^{th}$ day of each dosing period (Days 6, 12, and 18), twice the MED intensity of UV light will be administered to delineated sites on the subjects' buttocks. The irradiation at baseline (Day −1) should be administered at approximately the same time that irradiation is scheduled on Days 6, 12, and 18, which is at 2 hours post dose. Eight hours after UV irradiation, a skin punch biopsy will be taken from the UV exposure site. The end of confinement will be Day 19. The follow-up visit will occur 7-10 days (i.e. Day 25 to Day 28) following the last dose in Period 3. An early termination (ET) visit will occur within 10 days of the day of discontinuation.

The MED will be determined within 10 days of dosing in Period 1. It is recommended that MED be done earlier than Day −2 in case MED is unsuccessful on the first attempt. Confinement is not required for MED assessment.

Sixteen healthy qualified screened subjects with valid MEDs should report to the study center on Day −1 of Period 1 for baseline assessments (including 2×MED irradiation with biopsy), and to begin confinement.

Following scheduled check-in procedures, a skin test site will be delineated on the subject's upper buttock between the beltline and the natal cleft on right side. The test site will be minimum of 3 cm×3 cm, and will be outlined in ink (using a skin marker) with the subject lying prone. Subjects will receive 2×MED UV irradiation to one site on the buttock. One baseline skin punch biopsy will be taken from the UV-exposed site 8 hours (+/−10 minutes) after the UV-irradiation.

On Day 1, after a minimum 8 hours fast, subjects will receive the first dose of study drug at approximately 8 AM:
All subjects will receive the following doses of Compound 1 in the fixed sequence below:
Treatment A: 60 mg Compound 1 as active in capsule (AIC), QD×6 days, followed by
Treatment B: 160 mg Compound 1 AIC, QD×6 days, followed by
Treatment C: 400 mg of Compound 1 AIC, QD×6 days.
During each period, subjects may be domiciled at the study site starting on Day −1 (or as early as Day 2, if Baseline 2×MED is scheduled early in the day of Day −1), and will be discharged on Day 19 upon satisfactory safety review and after the completion of study-related procedures.

The study drug (as AIC) will be given orally with approximately 240 mL of noncarbonated water (at room temperature). The first meal following the morning dose on the 6$^{th}$ day of each dosing period will be 4 hours post dose. On all other dosing days, the next meal/snack can be served after a minimum 2 hours fast after dosing.

On Baseline (Day −1), Days 6, 12, and 18, the skin test sites will be delineated on the subject's upper buttock between the beltline and the natal cleft on right side. The right side of the buttock will be divided into three (3) different test sites, one positioned site for 2×MED irradiation at Baseline and at each of the 3 periods (Day 6, Day 12, and Day 18). Each test site will be as large as possible (minimum of 3 cm×3 cm). The test site areas will be outlined in ink (using a skin marker) with the subject lying prone.

Subjects will receive 2×MED UV irradiation to one site on the buttock 2 hours (+/−10 minutes) after administration of the study drug on Days 6, 12, and 18. Ultraviolet irradiation at Baseline should be scheduled approximately 2 hours after the planned dosing time for Day 1. It is suggested that the UV exposure sites be in sequential order starting with the extreme left and moving across to the extreme right (i.e. exposure site 1 for Baseline; and exposure site 4 for Period 3).

One skin punch biopsy will be taken from the UV-exposed site 8 hours (+/−10 minutes) after the UV-irradiation. Four biopsies will be taken throughout the study; ie. baseline and one biopsy per period. The biopsies will be processed into tissue slides by a third party to be designated by Celgene and analyzed by immunohistochemistry (ICH). This third party will be blinded to the treatment periods (Baseline and doses).

Subjects will be discharged from the clinical site on Day 19 after all scheduled procedures have been completed.

Adverse event (AE) monitoring, physical examinations, vital signs, electrocardiograms (ECGs), safety laboratory evaluation, and evaluation of wound healing will be performed at specified time points for safety assessments.

Serial blood samples will be collected at pre-defined time points (Days 6, 12, and 18: predose, 0.5, 2, 4, 6, 10, 12, and 24 hr postdose) for analysis of Compound 1 levels. All evaluations will be performed in accordance with the Table of Events and Procedures.

Procedures (except for the change in treatment) will be consistent across all 3 periods.

Activities, environment, food, procedures, and schedule between treatment periods should be kept as consistent as possible.

Part 2:

Part 2 will be an open label, randomized, cross-over study with 3 periods. The study will consist of a screening phase (Day −21 to −2), baseline (Day −1), 3 treatment/assessment periods, and a follow-up phone call.

Twelve eligible subjects will check into the study center on Day 1 of Period 1 for baseline assessments. On Day 1 of Period 1, subjects who continue to be qualified for participation in the study will be randomly assigned to one of three dosing sequences during which they will receive one of the following dosing regimens:

Treatment D: 2×100 mg Compound 1 as AIC, single oral dose administered under fasted conditions.

Treatment E: 1×200 mg Compound 1 (formulated tablet(s)) single oral dose administered under fasted conditions.

Treatment F: 1×200 mg Compound 1 (formulated tablet(s)) single oral dose administered under fed conditions (standard high fat breakfast).

TABLE 1

Food Effect Treatment Sequences

| Sequence | Period 1 | Period 2 | Period 3 |
|---|---|---|---|
| Sequence 1 | D | E | F |
| Sequence 2 | E | F | D |
| Sequence 3 | F | D | E |

All subjects will fast overnight for at least 10 hours prior to dosing. Subjects receiving Treatment D and E (fasted) will continue to fast for at least 4 hours after dosing.

For Treatment F, subjects will receive a standard high fat (approximately 50% of the total caloric content of the meal), high-calorie (approximately 800 to 1000 calories) breakfast within 30 minutes before dosing (based on FDA Center for Drug Evaluation and Research Food Effect Guidance, (FDA, 2002)). The meal should derive approximately 150, 250, and 500 to 600 calories from protein, carbohydrates, and fat, respectively. Subjects must consume the entire meal within 30 minutes of serving. Dosing must occur 30 minutes (±5 minutes) after serving the meal.

During each study period, subjects will be housed at the study center starting on Day −1. Subjects will be discharged from the study center on Day 5 of the last period upon completion of study procedures. Each treatment period will be separated by a washout period of at least 7 but no more than 10 days from the last Compound 1 dose to the next scheduled dose. Serial blood samples will be collected during each period at predose, 0.5, 1, 1.5, 2, 2.5, 3, 5, 8, 12, 24, 36, 48, 72, and 96 hours post dose to determine the levels of Compound 1 in plasma.

If necessary, subjects may leave the clinic following scheduled procedures on the morning of Day 5 of Periods 1 and/or 2, and return for the following period. In certain instances, a longer washout may be acceptable if mutually agreed upon.

Study Population.

Healthy male and female subjects. Sixteen subjects will be enrolled in Part 1. Twelve volunteers will be enrolled in Part 2. Subjects may only participate in either Part 1 or Part 2.

Length of Study.

Part 1: approximately 7 weeks (including screening). Part 2: approximately 6 weeks (including screening).

The End of Trial is defined as either the date of the last visit of the last subject to complete the study, or the date of receipt of the last data point from the last subject that is required for primary, secondary and/or exploratory analysis, as pre-specified in the protocol and/or the Statistical Analysis Plan, whichever is the later date.

Study Treatments.

Compound 1 as AIC (30 mg and 100 mg dose strengths) and formulated tablets (200 mg) will be supplied in bulk containers by Celgene.

Part 1: Treatment A (60 mg): 2×30 mg Compound 1 as AIC, QD×6 days; Treatment B (160 mg): 2×30 mg+1×100 mg Compound 1 as AIC, QD×6 days; Treatment C (400 mg): 4×100 mg Compound 1 as AIC, QD×6 days Part 2: Treatment D: Compound 1 2×100 mg as AIC (200 mg), given QD in the fasted state; Treatment E: Compound 1 as formulated tablets (1×200 mg), given QD in the fasted state; Treatment F: Compound 1, as formulated tablets (1×200 mg), given QD in the fed state Overview of Safety Assessments:

Safety will be monitored throughout the study. Safety evaluations will include adverse event (AE) reporting, PEs, vital signs, 12-lead ECGs, clinical laboratory safety tests (including liver function tests (LFTs), total cholesterol, triglycerides, high-density lipoprotein (HDL), and low-density lipoprotein (LDL)) in addition to standard clinical chemistry, hematology, and urinalysis tests), review of concomitant medications/procedures, evaluation of wound healing, and pregnancy tests for female subjects.

All AEs will be monitored and recorded throughout the study from the time the informed consent form (ICF) is signed until study completion, and when made known to the Investigator within 28 days after the last dose of Compound 1 (and those serious adverse events (SAEs) made known to the Investigator at any time thereafter that are suspected of being related to IP). All concomitant medications and procedures will be reviewed and recorded from the time the subject signs the ICF until study completion. A follow-up visit (Part 1) or a follow-up phone call (Part 2) will be scheduled for all subjects. If a subject is discontinued from the study for any reason, an ET visit will be performed.

Overview of Pharmacokinetic Assessments:

In both parts of the study, blood samples will be collected at specified times to determine plasma levels of Compound 1.

Part 1:

Collect blood/plasma on Day 6, 12, and 18: predose, 0.5, 2, 4, 6, 10, 12, and 24 hour post dose;

Plasma PK parameters at steady state including but not limited to the following: $AUC_\tau$ (Area under the plasma concentration-time curve from time zero to tau, where tau is the dosing interval); $C_{max}$ (Maximum observed plasma concentration), $C_{min}$ (Minimum observed plasma concentration), $T_{max}$ (Time to $C_{max}$).

Part 2:

Collect blood/plasma at each period: predose, 0.5, 1, 1.5, 2, 2.5, 3, 5, 8, 12, 24, 36, 48, 72, and 96 hours post dose.

PK parameters at steady state including but limited to the following: $AUC_{0-t}$, (Area under the plasma concentration-time curve from time zero to the last quantifiable concentration); $AUC_\infty$ (Area under the plasma concentration-time curve from time zero extrapolated to infinity); CL/F (Apparent total plasma clearance when dosed orally); $V_z$/F (Apparent total volume of distribution when dosed orally, based on the terminal phase); $t_{1/2}$ (Terminal-phase elimination half-life); $C_{max}$ (Maximum observed plasma concentration); and $T_{max}$ (Time to $C_{max}$).

Overview of Pharmacodynamic Assessments:

Individual ultraviolet B (UVB) exposure for MED determination:

UVB exposure within 10 days of first dosing in Period 1 consisting of UVB exposure to 6 sites on the left buttock with incrementally increasing UV intensity.

MED determination approximately 24 hours after UVB exposure.

Individual UVB exposure (2×MED):

At Baseline (Day −1) and on Days 6, 12, and 18: 2×MED UVB exposure to single site on upper buttock at 2 hours post Compound 1 dose.

Collection of biopsies: One punch biopsy (approximately 3 mm in diameter by approximately 0.8 mm in depth) from each test site will be collected at baseline (Day −1), and on Days 6, 12, and 18: eight (8) hours post UVB irradiation (a total of 4 punch biopsies).

Analysis of biopsy samples: Biopsies will be analyzed and phosphorylated c-Jun expression will be analyzed by Immunohistochemistry (IHC) assays. Other biomarkers such as, but not limited to, c-Jun, may be explored using the same skin biopsies and may be reported separately.

Phosphorylated c-Jun IHC data may be analyzed by either an analog scoring system or by an automated measurement of integrated optical density by trained individuals who are blinded to the treatments. For Part 1 only the Phosphorylated c-Jun IHC data will be subjectively scored on a scale of 0 to 4 based on the intensity and number of epidermal keratinocyte nuclei stained within the tissue section by trained individuals blinded to treatment.

6.3. Procedures for UV Irradiation

This section applies to subjects in Part 1 only.

Ultraviolet Radiation Source:

A DermaPal (manufactured by Daavlin) with a Kodacel filter (the UV lamp) will be used as the ultraviolet radiation source in this study. This lamp is chosen because it produces a similar spectrum to lamps used in previous validated studies documenting activation of JNK.

The same ultraviolet radiation source should be used during the study for UV-irradiation of all subjects.

A device will be attached to the UV lamp to ensure exposure only to the circumscribed areas. In addition, an appropriate shield will be used to avoid unnecessary exposure of other areas of the skin. The device will be documented in the source documents.

The spectral distributions of the optical output of the UV lamp should be calibrated before study start (by a third party) and these reports are maintained in the study files. A copy of the reports should be in the study files and should be referenced in the study report.

The details of ultraviolet radiation source will be documented in the source documents and the study report.

Determination of Minimum Erythema Dose (MED) of Unprotected Skin:

Within 7 days of enrollment in Period 1 (i.e. Days −7 to −1), six unprotected sites on the left buttock will be exposed to UVB in incrementally increasing UV intensity.

Measurement of UV Intensity:

Intensity measurement(s) will be taken before UV-exposure for MED determination and before UV-irradiation with 2×MED on Day 6 from the calibrated UV lamp.

The lamp should be warmed up for at least 15 minutes prior to use.

The measurement will be taken at the same distance from the lamp that the subject's skin would be during exposure. Intensity measurements will be documented in the source documents and recorded in the case report form (CRF).

Subjects should be lying on their stomachs during the exposure.

Six neutral 12.5 mm diameter density filters of absorbance: 0.0, 0.1, 0.2, 0.3, 0.4, and 0.5 will be mounted in an exposure plate attached directly to the DermaPal. This device will provide a series of UV intensities on the skin (e.g. 100.0%, 80.0%, 64.0%, 51.2%, 41.0% and 32.8%). The device will allow, with a single timed exposure, six (6) different UVB doses to be simultaneously delivered to the buttock of each subject.

The duration of exposure will be determined prior to study start based on Fitzpatrick skin type and documented as E minutes in the study records and the CRF.

The start and end time of exposure will be documented for each test site in source documents and CRF. The lamp distance from the subject will be consistent. The distance will be measured and documented in source documents and the CRF.

At approximately 24 hours (±1 hour) after the irradiation, the sites will be illuminated by a 100-watt incandescent white bulb and visually evaluated for erythema by a qualified evaluator.

The MED is the lowest UV dose that causes minimally perceptible skin reddening (i.e., produces uniform redness of the borders of the exposure site, erythema grade of 1, using the smallest dose of energy).

If, for example, the MED is determined to be the third exposure site, then the MED will be 64% of the total exposure (or 0.64×E minutes). In this example, a 2×MED exposure would be 2×0.64×E minutes. This will be the duration of exposure used for the remainder of the exposures for this subject.

If determination of a MED is not possible after initial exposure, subjects may be re-exposed once within 1 week from initial exposure, at a naive site in buttock. The duration for the new exposure should be within +35% of the duration of initial exposure.

Additional exposures may be performed at least one week apart if the subject will be re-screened (e.g., for a subsequent dosing cohort).

In order for MED to be valid:

a. At least one site out of the 6 exposed sites should meet the definition of minimally perceptible erythema; and b. This site cannot be the location with the lowest intensity of UV exposure.

A neutral density filter will not be used during the 2× exposure. MED for each subject and time of exposure will be documented in the source documents and the CRF.

The subjects may be confined for MED determination.

Erythema Grading Scale:

Erythema will be assessed 24 hours (1 hour) after UV exposure according to the following scale.

TABLE 2

Erythema Grading Scale for MED Determination

| Grade | Skin Appearance |
|---|---|
| 0 | No visible reaction |
| 0.5 | Slight, patchy erythema |
| 1 | Minimally perceptible skin reddening, uniform redness up to the borders of the exposure site (pink). This will be defined as MED. |
| 2 | Moderate erythema (definite redness) |
| 3 | Strong erythema (very intense redness) |

A number of references have been cited, the disclosures of which are incorporated herein by reference in their entirety.

What is claimed is:

1. A method for identifying a patient who is sensitive to 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof, comprising exposing a first portion of said patient's skin to UVB irradiation, obtaining a sample of said first portion of said patient's skin, measuring the amount of phosphorylated c-Jun in said first portion of said patient's skin, administering an effective amount of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof to said patient, exposing a second portion of said patient's skin to UVB irradiation at least about 2 hours after administration of said 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin indicates that said patient is sensitive to 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof, further comprising the administration of an effective amount of 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof to said patient who is sensitive to said 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof for the treatment of a disease or condition associated with c-Jun N-terminal kinase in said patient.

2. The method of claim 1, wherein 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof is administered in an amount of about 10 mg to about 1200 mg per day.

3. The method of claim 2, wherein 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof is administered in an amount of about 60 mg/day, about 160 mg/day or about 400 mg/day.

4. The method of claim 3, wherein 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof is administered orally.

5. The method of claim 4, wherein 2-(tert-butylamino)-4-((1R,3R,4R)-3-hydroxy-4-methylcyclohexylamino)-pyrimidine-5-carboxamide or a pharmaceutically acceptable stereoisomer, tautomer, solid form, polymorph, salt, hydrate, clathrate, or solvate thereof is administered in the form of a capsule or tablet.

6. The method of claim 1, wherein the disease or condition associated with c-Jun N-terminal kinase is a liver fibrotic disorder, steatosis, cirrhosis, primary sclerosing cholangitis, primary biliary cirrhosis, hepatitis, hepatocellular carcinoma, or liver fibrosis coincident with chronic or repeated alcohol ingestion, with infection, with liver transplant, or with drug induced liver injury.

* * * * *